United States Patent [19]
Stitt

[11] Patent Number: 4,857,326
[45] Date of Patent: Aug. 15, 1989

[54] STABLE NUTRITIVE AND THERAPEUTIC FLAX SEED COMPOSITIONS, METHODS OF PREPARING THE SAME, AND THERAPEUTIC METHODS EMPLOYING THE SAME

[76] Inventor: Paul A. Stitt, 123 Cleveland Ave., Manitowoc, Wis. 54220

[21] Appl. No.: 946,727

[22] Filed: Dec. 29, 1986

[51] Int. Cl.[4] .................. A61K 35/78; A61K 33/30
[52] U.S. Cl. .............................. 424/195.1; 424/145; 424/489; 424/502; 514/345; 514/552; 514/822; 514/937
[58] Field of Search ............ 424/195.1, 145, 489, 424/502; 514/345, 824, 937, 552

[56] References Cited

U.S. PATENT DOCUMENTS

| | | | |
|---|---|---|---|
| 3,163,545 | 12/1964 | Martin | 426/417 |
| 4,031,261 | 6/1977 | Durst | 429/565 |
| 4,073,947 | 2/1978 | Witt, Jr. | 426/13 |
| 4,180,595 | 12/1979 | Lauredan | 426/575 |
| 4,415,554 | 11/1983 | Horrobin | 424/145 |
| 4,543,264 | 9/1985 | Stahel | 426/629 |

OTHER PUBLICATIONS

U.S. Dispersatory 23rd Ed. 1943, pp. 601–602.
H. J. Klosterman et al., "Extraction of the Antipyridoxine Factor in Flax Cotyledons" *North Dakota Academy of Science*, vol. XIV, 1960.
Hartling, C., "Lein und Leinsamen, eine uralte Kulturpflanze, eine zu Unrecht Umstrittene Droge", *Deutsche Apotheker—Zeitung;* 109:27; 1025–1028 (Jul. 3, 1969) and translation thereof.
Brummer, J. N., "Leinsamen—seine Qualitatsmerkmale and ein moglicher Gehalt an Blausaure im Brot", *Brot und Geback*, 9:170–174 (1969) and translation thereof.

*Primary Examiner*—John W. Rollins
*Attorney, Agent, or Firm*—Sughrue, Mion, Zinn, Macpeak & Seas

[57] ABSTRACT

A method for producing a stable dry composition of flax seed comprising grinding the flax seed in the presence of vitamin B-6 and zinc ion at a temperature of about 160° F. to just above freezing. A stable dry composition of flax seed producted by the aforementioned method. A method for producing a stable emulsion or suspension of flax seed comprising: (1) grinding the flax seed in the presence of vitamin B-6 and zinc ion at a temperature of about 160° F. to just above freezing; (2) soaking the flax seed in an aqueous solution for about 10 minutes to overnight at a temperature of about 160° F. to just above freezing; and (3) blending or homogenizing said soaked, ground flax seed, with or without further additives, to form a stable emulsion or suspension; provided that the steps (1) and (2) can be conducted in any order. A stable emulsion or suspension of flax seed. A method of lowering serum triglycerides and/or cholesterol comprising administering a therapeutically effective amount of the stable emulsion or suspension of flax seed. A method of treating the symptoms of psoriasis comprising administering topically to an affected area the stable emulsion or suspension of flax seed.

49 Claims, No Drawings

STABLE NUTRITIVE AND THERAPEUTIC FLAX SEED COMPOSITIONS, METHODS OF PREPARING THE SAME, AND THERAPEUTIC METHODS EMPLOYING THE SAME

FIELD OF THE INVENTION

The present invention relates to stable nutritive and therapeutic flax seen compositions, methods of preparing the same and therapeutic methods employing the same. More particularly, the present invention relates to an edible stable emulsion or suspension of flax seed, an edible stable dry composition of flax seed, methods for preparing the emulsion or suspension and dry composition, a method of lowering serum triglycerides and/or cholesterol by administering a therapeutically effective amount of the stable flax seed emulsion, and a method of treating the symptoms of psoriasis comprising topical administration of the flax seed emulsion or suspension.

BACKGROUND OF THE INVENTION

Numerous attempts have been made to prepare nutritive compositions containing linolenic acid (C 18:2) (hereinafter also referred to as Omega-3). Omega-3 is an essential fatty acid found in fish oil and linseed (flax seed) oil and has been implicated as possibly being important in preventing various human health disorders including heart trouble. Typically, the resultant compositions containing Omgea-3 also contain either fish oil or linseed oil and lack human consumption appeal.

Heart trouble is one of the leading causes of death in the United States. Various researachers have established that Omega-3, an essential oil found in fish and flax seed and a few other sources, is an effective preventive agent for athlersclerosis and thrombosis, two major types of heart trouble. Bang HO, Dyerberg J: Lipid metabolism and ischemic heart disease in Greenland Eskimos, *Adv. Nutr. Res.* 1980;3:1–22; Walsh GP: a GP's use of omega-3 lipids in coronary heart disease, *Br. J. Clin. Pract.* 1984; 31(symp. suppl.):75–76; Harris WS: Health effects of omega-3 fatty acids, *Contemp. Nutr.* 1985;10(August):1–2; Harris WS, Connor WE, Inkeles SB, et al; Dietary omega-3 fatty acids prevent carbohydrate-induced hypertriglyceridemia, *Metabolism* 1984,33:1016–1019.

Omega-3 is believed, but not definitely established, to prevent heart trouble by acting as an agent to transport cholesterol out of the body, by inhibiting the production of the highly undesirable low density lipoproteins, and by producing postacyclin PGI-3 which prevents unwarranted clotting of the blood platelets. Goodnight SH Jr. Harris WS, Connor WE: The effects of dietary 13 fatty acids on platelet composition and function in man: A prospective, controlled study, *Blood* 1981;58:880–885; Siess W. Roth P, Scherer B. et al: Platelet-membrane fatty acids, platelet aggregation, and thromboxane formation during a mackerel diet, *Lancet* 1980;1:441–444; Illingworth Dr, Harris WS, Connor WE: Inhibition of low density lipoprotein synthesis by dietary omega-3 fatty acids in humans, *Arteriosclerosis* 1984;4:270–275; Sanders TAB, Roshanai F: The influence of differenct types of 13 polyunsaturated fatty acids on blood lipids and platelet function in healthy volunteers, *Clin. Sci.* 1983;64(January):91–99; Cartwright I. J., Pockley A.G., Galloway J. H. et al: The Effects of dietary N-3 polyunsaturated fatty acids on erthrocyte membrane phospholipids, erthrocyte deformability and blood viscosity in healthy volunteers, *Atherosclerosis* 1985;55:267–281; Needleman P., Raz A., Minkes MS., et al; Triene prostaglandins: Prostacyclin and thromboxane biosynthesis and unique biological properties, *Proc. Natl. Acad. Sci. USA* 1979;76;944–948.

For these and other reasons, finding, utilizing, and putting as many sources of Omega-3 as possible into the American food chain is highly desirable to prevent the pain, suffering, and medical costs associated with heart trouble in the United States.

One major source of Omega-3 currently in use is fish oil. The concentration of Omega-3 in fish is rather low, but when the fish oil is extracted from the fish it contains most of the Omega-3. However, the flavor is rather undesirable for use in foods or drinks. Fish oils are also very high in calories and cholesterol content and are difficult for the human body to disgest.

The other major source of Omega-3 is linseed oil. For many years it has been known that Omega-3 is available in linseed oil, which is made from flax seed. However, the flavor due to its oxidation makes the linseed oil highly undesirable for human consumption.

Flax seed is an ideal source of Omega-3 for humans. It is very abundant and the seeds have a rather sweet, nutty taste. The present drawback to using flax seed to obtain Omega-3 for consumption is the rate at which the Omega-3 turns rancid. When linolenic acid is normally extracted from flax seed to make linseed oil paint, it turns rancid very rapidly. Rancid linseed oil is highly toxic to humans.

Currently, linseed oil for human consumption is derived either by high temperature and high pressure or by high temperature grinding and solvent extraction of flax seed.

Either method produces a product which has a highly undesirable flavor and also contains rancid products that may be toxic to humans. Flax seed compositions also tend to produce cyanide during preparation as well as storage and consumption. Bruemmer found that crushed linseed produced 18 mg of HCN per hour at room temperature (J. M. Bruemmer, *Brot Gebaeck*, 29 (9), 170–174 (1969) (Ger).

As an example of preparing flax seed for human consumption, U.S. Pat. No. 4,180,595 discloses the use of dry linseed along with other ingredients in formulations of a milk-containing drink. In this patent, water, gum arabic, dry linseed, in an amount of 0.5 to about 0.8 part by weight, per 100 parts by weight of water, and seamoss are first combined and heated to boiling, followed by filtering and blending with milk and sweetening agents.

Further, U.S. Pat. No. 4,073,947 discloses the use of whole linseed to provide a protein hydrolyzate for use in beer-type beverages. The hydrolysis involves treating the whole linseed in water at 50°–52° C., with enzyme or acid to solubilize the protein. The hydrolyzate is then added to converted and buffered starch and boiled for 20 to 40 minutes.

U.S. Pat. No. 4,543,264 contemplates the use of a high protein concentrate of a particulate oil seed, which can be lineseed, to make a high protein supplement for food products. The high protein concentrate is produced by a process involving the steps of mixing the particulate oilseed material with water and a lower alcohol, heating with steam at a temperature of at least more than 190° F. and then drying.

Thus the processes for preparing the products of U.S. Pat. Nos. 4,180,595, 4,073,947 and 4,543,264 all involve treating the linseed at some point at temperatures in excess of 160° F. Thus the processes involve large inputs of energy.

U.S. Pat. Nos. 3,163,545 and 4,031,261 disclose the use of linseed oil in preparing foodstuffs and making milkshake-type products, respectively. Neither of these two patents discloses the use or incorporation of whole ground flax seed in preparing or making the food.

The present invention is also directed to a method of treatment for lowering serum triglycerides and/or choleserol.

Currently, many such treatments involve the administration of drugs.

However, considerable controversy exists concerning the use of drugs to lower serum triglycerides and/or cholesterol. This is because the side effects of the drugs are not inconsequential and are, apparently, sometimes worse than having high serum lipids. Further, some of the drugs used to treat the side effects of the lipid drugs are not so innocuous either. Therefore, if some other treatment program could be found to lower serum lipids without causing adverse side effects, it would be of double benefit—no side effects from the drug used to treat serum lipids and no side effects from the drug used to treat the side effects from the primary drug.

As an alternative to treatment with drugs there is treatment with fish oils. However, fish oils are poorly absorbed and are in limited supply, and the flavor of fish oil in drinks is not liked by many people.

Thus an alternatie treatment to the use of drugs or fish oils would be desirable.

The present invention is also directed to a new method for treating the symptoms of psoriasis.

SUMMARY OF THE INVENTION

Accordingly, one object of the present invention is to provide a stable dry composition of flax seed which can be used to prepare various tasty foodstuffs suitable for animal and human consumption and which are high in nutritive value, including essential fatty acids, especially Omega-3.

A second object of the present invention is to provide a method for producing the above-described stable dry composition of flax seed, which method involves the use of less energy input than currently known methods.

A third object of the present invention is to provide a stable emulsion or a suspension of flax seed which can be used for preparing tasty foodstuffs, especially drinks, yogurt and puddings which are suitable for animal and human consumption and which are high in nutritive value including essential fatty acids, especially Omega-3.

A fourth object of the present invention is to provide a method for producing the above-described stable emulsion or suspension of flax seed which involves less expenditure of energy than is used in the current methods.

A fifth objects of the invention is to provide a method for producing an emulsion or suspension of Omega-3 with a very small particle size so that the Omega-3 is easily and quickly absorbed by the body.

A sixth object of the present invention is to provide Omega-3 in a stable dry composition so that it is easily and quickly digested in the human body.

A further object of the present invention is to provide a flax seed composition which minimizes the content of cyanide.

An even further object of the present invention is to provide a method of lower serum triglycerides and/or cholesterol which does not have the serious side effects of drug administration; which involves the use of flax seed which can be made available in unlimited quantities; which is more efficient at lowering serum triglycerides and/or chloesterol than administration of fish oil; and which has a flavor that is liked by most people.

A still further object of the present invention is to provide a method of treating the symptoms of psoriasis.

These and other objects have been attained by providing a stable dry composition of ground flax seed which remains stable for up to six months and a method for producing the stable dry composition of flax seed which comprises grinding the flax seed in the presence of vitamin B-6 and zinc ion at a temperature of about 160° F. to just above freezing.

The present invention also provides a stable emulsion or suspension of flax seed and a method for producing the stable emulsion or suspension of flax seed which comprises:

(1) grinding the flax seed in the presence of vitamin B-6 and zinc ion at a temperature of about 160° F. to just above freezing;

(2) soaking the flax seed in an aqueous solution for about 10 minutes to overnight at a temperature of about 160° F. to just above freezing; and (3) blending or homogenizing said soaked, ground flax seed, with or without further additives, to form a stable emulsion or suspension;

provided that the steps (1) and (2) can be conducted in any order.

A stable emulsion or suspension of flax seed consisting essentially of ground flax seed, vitamin B-6, zinc ion, and an aqueous solution which remains chemically and physically stable for one week to at least three months and a stable emulsion or suspension of flax seed comprising ground flax seed, vitamin B-6, zinc ion and an aqueous solution, wherein fat gobules in the emulsion or suspension have a size in the range of about 2.0 $\mu$ or less are also provided.

In a further embodiment, the present invention provides a method of lowering serum triglycerides and/or cholesterol comprising administering a therapeutically effective amount of a stable emulsion or suspension of flax seed described above.

In still another embodiment, the present invention provides a method of treating the symptoms of psoriasis comprising administering topically to an affected area the stable emulsion or suspension of flax seed described above.

DETAILED DESCRIPTION OF THE INVENTION

The stable dry composition of flax seed according to the present invention is produced by a method such that a whole ground flax seed results which can be kept for six months or longer with no signs of rancidity, i.e. the composition is chemically stable. This is entirely unexpected. The composition also is especially high in available Omega-3 and is such that the Omega-3 is more easily and quickly digested in the human body as compared to Omega-3 in other dry compositions containing whole ground flax seed.

The method for producing the stable dry composition of flax seed comprises a grinding the flax seed in the presence of vitamin B-6 and zinc ion at a temperature of about 160° F. to just above freezing.

Grinding is necessary so that the Omega-3 present in the seed is made available to the body in the digestive system.

According to the present invention, the flax seed is ground until the ground flax seed has a size of about 1/10 inch to 1/100 inch in diameter. A diameter of about 1/50 to 1/100 inch is especially preferred.

In order to grind the flax seed, any method can be used as long as the proper six ground flax seed is produced and as long as the temperature can be maintained at about 160° F. to just above freezing.

Suitable methods of grinding the flax seed can readily be determined by those skilled in the art and include the use of grinders such as a hammer mill, impact grinder or Alpine® grinder (manufactured by Alpine American Corporation, Natick, Massachussets).

Further according to the present method for producing a stable dry composition of flax seed, vitamin B-6 must be present during the grinding period.

Without wanting to be bound by any particular explanation, it is believed that the vitamin B-6 is needed in order to allow the Omega-3 to be metabolized by the human body or other animal body, particularly since flax seed is believed to contain an anti-vitamin B-6 factor.

The vitamin B-6 should be added in the form of a dry powder and thoroughly mixed with the ground flax seed. The vitamin B-6 is readily available commercially.

Further according to the present method, the vitamin B-6 should be added in an amount sufficient to allow the Omega-3 to be metabolized by the human body. This can readily be determined by one skilled in the art, for example, by checking urine for excess vitamin B-6.

A suitable amount of vitamin B-6 in the composition ranges from about 1 to 500, preferably 50 to 200, and more preferably 75 to 150 parts per million parts of flax seed.

An especially preferred amount of vitamin B-6 is about 100 parts per million parts of the flax seed.

Further according to the present invention, zinc ion must also be present during the grinding.

While not wanting to be bound by any explanation, it is believed that the zinc ion is necessary in order to allow the human body or other animal body to metabolize the Omega-3.

The zinc ion can be added in various forms which can readily be determined by those skilled in the art. Suitable forms of zinc ion which can be used include zinc sulfate, zinc oxide and zinc chloride.

Zinc sulfate is preferred.

The amount of zinc ion to be added can readily be determined by the skilled artisan, for example, by checking serum levels of zinc.

A suitable amount of zinc ion in the composition is in the range of about 1 to 500, preferably 10 to 400, and more preferably 150 to 300 parts per million parts of flax seed.

A particularly preferred amount of zinc ion is about 150 parts per million parts of flax seed used.

In order to obtain the effects of the present invention, the grinding step must be conducted at a temperature of from about 160° F. to just above freezing, preferably 50° to 100° F., and more preferably 60° to 80° F.

A particularly preferred temperature is room temperature, i.e. about 68° F.

As is known to those skilled in the art, natural flax seed contains substances that can produce cyanide in a moist environment. Unexpectedly, the present inventor has found that the addition of vitamin B-6 during the grinding step reduces the amount of cyanide produced during manufacturing, processing, packaging and consumption.

Optimum conditions for reduction of cyanide production include adding the vitamin B-6 in the grinding step in an amount of about 50 to 250 parts per million parts of the flax seed and conducting the grinding at a temperature of about 68° F.

In producing the stable dry composition of flax seed according to te present invention, it is also possible to add other ingredients during or after the grinding step, so long as they do not interefere with the action of vitamin B-6 and zinc ion.

Examples of suitable additives include pantothenic acid in an amount of about 1 to 500, preferably 20 to 250, and more preferably 50 to 100 parts per million parts of flax seed; niacin in an amount of about 1 to 500, preferably 20 to 400, and more preferably 100 to 200 parts per million parts of flax seed; vitamin C in an amount of about 1 to 1000, preferably 20 to 500 and more preferably 100 to 300 parts per million parts of flax seed; and vitamin E in an amount of about 1 to 500, preferably 10 to 300, and more preferably 50 to 150 parts per million parts of flax seed.

Other suitable ingredients which can be added during or after the grinding step can be readily determined by those skilled in the art.

According to the method for producing a stable dry composition of flax seed of the present invention, the dry composition of flax seed can be stored without turning rancid for six months or more.

Storage can generally be at a temperature of up to about 70° C. and should desirably be under conditions of minimum oxygen, light, and moisture.

The optimum method of storing the ground flax seed composition is in a light proof, moisture proof, oxygen proof barrier container after all oxygen has been removed at 0° F. to −50° F.

Another method suitable for storing the ground flax seed composition is to package it in a tin foil-oxygen barrier bag with oxygen removed by flushing with 3 to 10 volumes of carbon dioxide or nitrogen.

The present stable dry composition can then be used to prepare various foodstuffs such as cookies, breads, muffins, candy bars, meat analogues, processed meats, nutritional drinks and can be sprinkled on salads, used in soups or can be eaten as is.

The dry composition of flax seed can also be used to produce the stable emulsion or suspension of flax seed according to the present invention, which will be described next.

The stable emulsion or suspension of flax seed of the prevent invention is produced by a specific process which results in an emulsion or suspension of flax seed which remains chemically stable, i.e. does not turn rancid, and physically stable, i.e. does not separate into components for long periods of time. If not pasteurized, the emulsion or suspension remains chemically and physically stable for as long as one week if stored from about just above freezing to about 50° F. If pasteurized, the emulsion or suspension remains physically and chemically stable for at least four weeks if stored from about 26° F. to about 40° F. The emulsion or suspension can also be sterilized. If sterilized, the emulsion or suspension remains physically and chemically stable for at least three months if stored from about 26° F. to about 100° F.

The emulsion or suspension ranges in texture from thick, sticky substance to a liquid having the consistency of milk and barely separates at all.

Unexpectedly, the emulsion or suspension of the present invention is also especially high in available Omega-3 and is such that the Omega-3 is more easily and quickly digested in the human body as compared to Omega-3 in heretofore known liquid compositions containing fish oils or flax seed (linseed) oil. This is believed to be due to the size of the fat globules in the emulsion or suspension after blending or homogenizing which will be described below.

Specifically, the size of the fat globules in the emulsion or suspension after blending in the presence of an aqueous solution is in the range of from about 0.05 to 2.0 $\mu$. The size of the fat globules in the emulsion or suspension after homogenization can be even smaller than 0.05 $\mu$. This is in contrast to the size of the fat globules in blended fish oils which is in the range of from about 20 $\mu$ to 500 $\mu$.

The unpasteurized emulsion can be stored at any temperature from just above freezing to about 50° F., and the pasteurized emulsion can be stored at any temperature from about 26° F. to about 40° F. A preferred storage temperature is about 34° F. The sterilized emulsion can be stored at any temperature from about 26° F. to about 100° F. A preferred storage temperature is about 72° F.

The method for producing the stable emulsion or suspension of flax seed comprises:

(1) grinding the flax seed in the presence of vitamin B-6 and zinc ion at a temperature of about 160° F. to just above freezing;

(2) soaking the flax seed in an aqueous solution for about 10 minutes to overnight at a temperature of about 160° F. to just above freezing; and (3) blending or homogenizing said soaked, ground flax seed, with or without further additives, to form a stable emulsion or suspension;

provided that the steps (1) and (2) can be conducted in any order.

Thus, the method of the present invention for producing a stable emulsion or suspension of flax seed involves three steps, the first two of which can be conducted in either order. Then the third step is performed.

If the grinding step is conducted first, i.e., before any aqueous solution is present, the grinding is conducted in the same manner as the above-described method for producing a stable dry composition of flax seed.

If, on the other hand, the grinding step is conducted after the soaking step, the above-described conditions for the method for producing the stable dry composition apply, except that the grinding can also be carried out in an apparatus that is suitable for grinding wet flax seed, such as a blender. However, as with grinding dry flax seed, a hammer mill, impact grinder, or Alpine Grinder ® can also be used to grind the wet flax seed.

In either case, the grinding is carried out until the ground flax seed has a size of about 1/10 inch to 1/1000 inch diameter.

For making the emulsion, the flax seed is used in an amount of from about 1 to 25 parts by weight per 100 parts by weight of the aqueous solution used in step (2), preferably from about 3 to 20 parts by weight per 100 parts by weight of the aqueous solution used in step (2), and more preferably from about 6 to 12 parts by weight per 100 parts by weight of the aqueous solution used in step (2).

For conducting the soaking step, the solution in which the flax seed is soaked can be any aqueous solution. Suitable solutions include water, milk, fruit juice (e.g. orange, grape, apple, blackberry strawberry), vegetable juice (e.g. carrot, beet, celery, tomato), etc.

Preferred solutions include water, orange juice, tomato juice, and apple juice. Water is especially preferred.

In order to obtain the effects of the present invention, it is necessary that the soaking be conducted for at least about 10 minutes before the emulsion is consumed.

However, soaking can be conducted for an amount of time of from about 10 minutes to overnight (about 12 hours). A preferred amount of time for soaking is about 15 to 60 minutes, and a more preferred amount of time for soaking is about 20 to 30 minutes. An especially preferred amount of soaking time is about 20 minutes.

Further, as with the grinding step, the soaking step must be conducted at a temperature of about 160° F. to just above freezing. A preferred temperature range is from about 40° to 80° F., and a more preferred temperature range is from about 50° to 70° F. An especially preferred soaking temperature is about room temperature (about 68° F.).

After grinding and soaking the flax seeds, the resultant mixture is either blended or homogenized, with or without further additives, to form a stable emulsion or suspension of flax seed.

The blending or homogenizing is carried out until an emulsion or suspension having the desired consistency and/or texture is obtained. Depending upon the amount of liquid present, the emulsion or suspension will range in texture from a thick, sticky substance to a creamy smooth substance, similar in consistency to conventional milk.

The blending is accomplished with any equipment suitable for thoroughly mixing the mixture to form an emulsion or suspension. For example, a conventional kitchen blender can be used.

Homogenization is carried out by conventional methods, such as for example by using a Cherry-Burrel ®, (Registered Trademark of Cherry-Burrell Corporation of Cedar Rapids, Iowa, 52406), two stage homogenizer. The flax seed mixture is soaked at 120° F. for 30 minutes and then passed through Stage 1 at 500 PSI five times. This is followed by passing the mixture through Stage 2 at 3500 PSI two times.

After blending or homogenizing, the emulsion or suspension can be consumed or used immediately or stored for later use or consumption. If not pasteurized, the product can be stored for at least one week at temperatures of from about just above freezing to about 50° F. The product can also be pasteurized to kill most organisms naturally present in the flax seed or be sterilized to kill all organisms in the emulsion or suspension in order to prolong shelf life. When stored at temperatures of from about 26° F. to about 40° F., the pasteurized product remains stable for at least four weeks. When stored at temperatures of from about 26° F. to about 100° F., the sterilized product remains stable for at least three months.

Pasturization is carried out according to methods known in the art, for example by heating at 180° F. for twenty minutes or at 280° F. for 21 seconds. Then the product is immediately cooled to 32° F.

Sterilization is carried out according to methods known in the art, for example by heating at 250° F. for 15 minutes.

As already mentioned, the stable emulsion or suspension of flax seed thus produced can be consumed or used as is or various additives can be included. Such additives include milk; various meats; one or more fruits, nuts, vegetables and seeds; various nutrients; various flavorings; various sweetening agents; artificial colors certified for human or animal consumption; anti-oxidants; texture improvers; fillers; preservatives; and the like. Further, a yogurt inoculum can be added to make a yogurt product.

The additives are used in amounts readily determined by those skilled in the art.

Further, if the additives are dry, they may be added at any time during the method. However, if the additives are moist, such as fruit, or are liquid in nature, they are preferably added during the soaking step, but can also be added during or after the blending or homogenizing step.

As examples of suitable milks there are 1%, 2% and whole milk.

The milk drink can be made by adding one part to 10 parts by weight of the flax seed emulsion or suspension to 1%, 2% or whole milk, mixing thoroughly, homogenizing, and then pasteurizing.

As examples of suitable meats there are frankfurters, summer sausage and kielbasa.

The meats can be added to produce processed meat products or meat analogues. The processed meat products or meat analogues are produced by methods known to those skilled in the art, such as for example by adding 5 parts by weight to the flax seed emulsion or suspension to 100 pounds of meat or a mixture of meat and meat analogue, grinding and mixing thoroughly, stuffing the mixture into casings, smoking at 100° F. for 36 hours, and then heating until the internal temperature reaches 160° F.

Suitable amounts of the emulsion or suspension to be added to the meat include about 1 to about 20 parts by weight of emulsion or suspension, preferably about 5 to about 15 parts by weight of emulsion or suspension, and more preferably about 10 parts by weight of emulsion or suspension to about 100 parts by weight of meat.

As examples of suitable fruits, there are oranges, mangos, apples, bananas, papayas, pineapples, strawberries, etc.

As examples of suitable nuts, there are almonds, pecans, walnuts, cashews, hickory nuts, etc.

As examples of suitable seeds, there are sesame seeds, sunflower seeds, etc.

As examples of suitable vegetables there are carrots, celery, beets, etc.

A suitable amount of fruits, nuts, vegetables, and seeds to be added is up to about 50 parts by weight per 100 parts by weight of solution used in step (2), for each fruit, nut, vegetable and/or seed added.

As examples of suitable nutrients, there are vitamins and/or mineral mixtures, egg whites (dried or fresh), soy protein, and dried milk.

A suitable amount of nutrient mixture to be added to the emulsion is about 0.1 to 10 parts by weight per 100 parts by weight of solution used in step (2).

Especially preferred nutrients are egg whites, dried milk and/or soy protein. The egg whites can be dried egg whites or fresh egg whites and suitable amounts to be used are about 2 parts and 10 parts by weight, respectively, per 100 parts by weight of solution used in step (2). A suitable amount of soy protein to be added is from about 1 to 10 parts by weight per 100 parts by weight of solution used in step (2). A suitable amount of non-fat dried milk to be added is from about 1 to 10 parts by weight per 100 parts by weight of solution used in step (2).

Suitable examples of flavorings include herbs, spices, vanilla, cinnamon, carob, nutmeg, etc.

A suitable amount of flavoring to be added is about 0.1 to 10 parts by weight per 100 parts by weight of solution used in step (2).

Suitable sweetening agents include honey and/or sugar, etc., and these are suitably added in an amount of up to about 20 parts by weight per 100 parts by weight of solution used in step (2).

Addition of sweeteners before and after pasteurization can be used to make a delicious pudding as follows. The ingredients comprise 20 parts by weight soy milk; 10 parts by weight flax emulsion (sticky emulsion—1 part flax seed, 3 parts water); 5 parts by weight whole eggs; 3 parts by weight arrowroot powder; ½ parts by weight vanilla; 10 parts by weight fructose; and 2 parts by weight coarse coconut. The ingredients are blended at high speed in a blender for 1½ minutes, baked at 300° F. for 30 minutes and then cooled.

To prepare the yogurt product, a yogurt inoculum is added after cooling to a pasteurized emulsion or suspension comprising 1 part by weight flax seed to 6 parts by weight water combined with an an equal volume of pasteurized soy milk or cow's milk. The inoculated product is then incubated according to methods known in the art, for example, by incubation for 6 hours at 80° F. to produce yogurt.

According to the present invention, there is also provided a method of lowering serum triglycerides and/or cholesterol which comprises administering a therapeutically effective amount of a stable emulsion or suspension of flax seed described above. The stable emulsion or suspension can be produced by the method described above.

In order to achieve the effect of lowering serum triglycerides and/or cholesterol, the stable emulsion or suspension of flax seed is administered orally to an adult or child in an amount equivalent to about 2 to 100 gram of dry flax seed per day. A preferred dosage range is about 5 to 65 grams of dry flax seed per day, and a more preferred dosage range is about 15 to 50 grams of dry flax seed per day.

According to the present invention, there is also provided a method of treating the symptoms of psoriasis which comprises administering topically to an affected area the stable emulsion or suspension of flax seed described above.

The stable emulsion or suspension of flax seed can be produced by the method described above, but for practical purposes, the third step usually comprises blending, rather than homogenizing, the soaked ground flax seed, and, of course, optional further additives included for taste are not especially contemplated. Also additives that might irritate the skin would not be included.

For example, a suitable emulsion or suspension can be prepared by soaking two tablespoons of ground flax seed produced according to step (1) of the above described method in 1 cup of water for about 30 minutes at room temperature, i.e., about 68° F., and then blending in a conventional blender for two minutes.

The treatment involves topically applying the stable emulsion or suspension of flax seed to the affected area by smearing a thin layer or film of the emulsion or suspension of the skin.

The amount of time the emulsion or suspension should be kept in contact with the affected area will vary with the severity of the symptoms and can readily be determined by those skilled in the art. However, a suitable amount of time is generally in the range of about 12 hours.

The treatment totally or partially relieves the symptoms, i.e., itchiness and scabiness, of psoriasis.

The invention will now be described by reference to specific examples which are not in any away meant to be limiting.

Unless otherwise specified, all percents, ratios, and parts, etc., are by weight.

EXAMPLES

EXAMPLE 1

Preparation of Tasty Natural Drink

Whole flax seed with 100 ppm vitamin B-6 and 100 ppm zinc sulfate added was ground in a hammer mill grinder with ⅛" screen. The dry fortified ground flax seed was found to be stable for over six weeks with no significant cyanide or rancid products formed. Fifteen parts of the resultant fortified flax seed was added to 100 parts of water at room temperature and then was allowed to stand for ten minutes. The two parts of dried egg white or ten parts fresh egg whites were added plus on skinned banana. The mixture was blended at high speed for one minute. The product was found to be a delicious natural drink.

EXAMPLE 2

Preparation of A tasty Flax Yogurt

Fifteen parts of fortified ground flax seed composition was added to 100 parts water and allowed to soak for 20 minutes. Then the mixture was stirred and pumped through a standard dairy homogenizer four times. The resultant product was a tan colored cream. Then the emulsion was pasteurized through a standard dairy pasteurizer, then cooled, inoculated with a standard yogurt culture and allowed to incubate at 85° for eight hours. Then blueberries were added to make a delicious all-flax creamy yogurt.

EXAMPLE 3

Preparation of A Creamy Orange Drink 1 part ground fortified flax seed composition to 5 parts orange juice were soaked for 10 minutes at 90° F. These ingredients were then blended at high speed for 20 seconds. A delicious creamy range drink resulted.

EXAMPLE 4

Preparation Of A Carrot Drink 40 parts of fortified ground flax seed were added to 100 parts water and soaked overnight at 35° F. After 16 hours, the mixture was blended with equal parts carrot juice for 40 seconds. The result was a delicious thick carrot juice.

EXAMPLE 5

Treatment of Persons With High Serum Lipids

In order to demonstrate the ability of the present emulsion or suspension to lower serum triglycerides and/or cholesterol, one person having normal serum lipids and six persons having high serum lipids and/or cholesterol or indications thereof, were treated according to the method of treatment of the present invention.

The fortified flax seed emulsion or suspension used for each subject was prepared as follows:

25000 grams of flax seed was ground at 68° F. in the presence of 100 ppm vitamin B-6 and 50 ppm zinc sulfate in a hammer mill with ⅛" screen to a size of 1/10 to 1/1000 inch in diameter. 17 grams of ground flax seed was soaked for 20 minutes in 8 ounces of water at 80° F. The ground, soaked flax seed was then blended for 45 seconds in a Warning blender ® at high speed.

The method used for determining serum triglycerides and/or cholesterol were those prescribed by the American Association of Organic Chemists.

Subject No. 1, who had athlersclerosis, was treated with Capotin ® for one year with no change in the circulation in his legs. Then he was treated for two months with high potency cod lever oil, but still no change in circular was observed. Then he was treated with the above-described fortified flax seed emulsion at a dosage of 700 ml per day (50 grams of dry flax seed per day), and in six weeks his legs and feet felt warmer. After taking the flax seed emulsion for six weeks, his cholesterol was 8% lower and triglyceride was 40% lower than it was 8 months before he started the program. The most significant finding in this case was that the patient regained circulation in his legs six weeks after starting to take the fortified flax seed emulsion.

Subject No. 2 was administered the above-described fortified flax seed emulsion at a dosage of 100 ml per day (17 grams of dry flax seed per day). The subject had a cholesterol drop of 14% after taking the flax seed emulsion for 3 months.

Subject No. 3 was administered the above-described fortified flax seed emulsion at a dosage of 200 ml per day (34 grams of dry flax seed per day). The subject had a drop in triglycerides from 463 to 348 mg per deciliter (25% drop) in four weeks, and his cholesterol level was 152 mg per deciliter compared to a 174 average for the previous year.

Subject No. 4 was administered the above-described foritified flax seed emulsion at a dosage of 200 ml per day (34 grams of dry flax seed per day). This subject had normal cholesterol and triglyceride levels before starting to take the flax seed emulsion. After participating in the program for nine months, his prothrombin time was still in the normal range. This indicates that ground flax seed does not excessively prolong bleeding times as has been found in some cases with fish oils.

Subject No. 5 was administered the above-described fortified flax seed emulsion at a dosage of about 10 ounces three times per day. (60 grams of dry flax seed per day). The patient had a blood pressure of 215/120. After 30 days of treatment, the patient's blood pressure was 140/90. There were no other changes in the patient's diet.

Subject No. 6 had severe angina pain. After taking the above-described fortified flax seed emulsion or suspension at a dosage of 24 ounces per day he experienced no pain.

Subject No. 7 at age 27 had a triple heart bypass operation. His father had died at age 35 from a heart attack. After the operation the subject had a cholesterol level of 400 mg per deciliter and could not tolerate any medicine. The subject went on a severely fat limited diet plus 50 grams of dry flax seed per day in the form of the above-described fortified flax seed emulsion. In three weeks his cholesterol level was reduced to 220 mg per deciliter. Since his high cholesterol level was considered inherited, this was much better than expected.

While the invention has been described in detail and with reference to specific embodiments thereof, it will be apparent to one skilled in the art that various changes and modifications can be made therein without departing from the spirit and scope thereof.

What is claimed is:

1. A method for producing a stable dry composition of flax seed comprising grinding said flax seed in the presence of vitamin B-6 and zinc ion at a temperature of about 160° F. to just above freezing.

2. A method of claim 1, wherein said grinding is carried out until said ground flax seed has a size of about 1/10 inch to 1/1000 inch in diameter.

3. A method of claim 1, wherein said grinding temperature is 68° F.

4. A method of claim 1, wherein said vitamin B-6 is present in an amount of about 1 to 500 ppm parts of said flax seed and said zinc ion is present in an amount of about 1 to 500 ppm parts of said flax seed.

5. A method of claim 1, wherein said vitamin B-6 is present in an amount of about 50 to 250 ppm parts of said flax seed and said grinding temperature is about 68° F.

6. A stable dry composition of flax seed produced by a method comprising grinding said flax seed in the presence of vitamin B-6 and zinc ion at a temperature of about 160° F. to just above freezing.

7. A stable dry composition of claim 6 wherein said grinding is carried out until said ground flax seed has a size of about 1/10 inch to 1/1000 inch in diameter.

8. A stable dry composition of claim 6, wherein said grinding temperature is about 68° F.

9. A stable dry composition of claim 6, wherein said vitamin B-6 is present in an amount of about 1 to 500 ppm parts of said flax seed and said zinc ion is present in an amount of about 1 to 500 ppm parts of said flax seed.

10. A stable dry composition of claim 6, wherein said vitamin B-6 is present in an amount of about 50 to 250 ppm parts of said flax seed and said grinding temperature is about 68° F.

11. A stable dry composition of ground flax seed which remains stable for at least six months at a temperature of up to about 70° F.

12. A stable dry composition of flax seed comprising ground flax seed, vitamin B-6 and zinc ion, wherein the composition remains chemically stable for at least six months.

13. A method for producing a stable emulsion or suspension of flax seed comprising:
    (1) grinding said flax seed in the presence of vitamin B-6 and zinc ion at a temperature of about 160° F. to just above freezing;
    (2) soaking said flax seed in an aqueous solution for about 10 minutes to overnight at a temperature of about 160° F. to just above freezing; and
    (3) blending or homogenizing said soaked, ground flax seed, with or without further additives, to form a stable emulsion or suspension;
    provided that the steps (1) and (2) can be conducted in any order.

14. A method of claim 13, wherein said flax seed is used in an amount of from about 1 to 25 parts by weight per 100 parts by weight of said solution used in said step (2).

15. A method of claim 13, wherein said grinding is carried out until said ground flax seed has a size of about 1/10 inch to 1/1000 inch in diameter.

16. A method of claim 13, wherein said grinding temperature is about 68° F.

17. A method of claim 13, wherein said vitamin B-6 is present in an amount of about 1 to 500 ppm parts of said flax seed and said zinc ion is present in an amount of about 1 to 500 ppm parts of said flax seed.

18. A method of claim 13, wherein said vitamin B-6 is present in an amount of about 50 to 250 ppm parts of said flax seed and said grinding temperature is about 68° F.

19. A method of claim 13, wherein said solution is selected from the group consisting of water, milk, fruit juice, and vegetable juice.

20. A method of claim 19, wherein said solution is water.

21. A method of claim 13, wherein said soaking is for about 20 minutes.

22. A method of claim 13, wherein said soaking temperature is about 68° F.

23. A stable emulsion or suspension of flax seed produced by a method comprising:
    (1) grinding said flax seed in the presence of vitamin B-6 and zinc ion at a temperature of about 160° F. to just above freezing;
    (2) soaking said flax seed in an aqueous solution for about 10 minutes to overnight at a temperature of about 160° F. to just above freezing; and
    (3) blending or homogenizing said soaked, ground flax seed, with or without further additives, to form a stable emulsion or suspension;
    provided that the steps (1) and (2) can be conducted in any order.

24. A stable emulsion or suspension of claim 23, wherein said flax seed is used in an amount of from about 1 to 25 parts by weight per 100 parts by weight of said solution used in said step (2).

25. A stable emulsion or suspension of claim 23, wherein said grinding is carried out until said ground flax seed has a size of about 1/10 inch to 1/1000 inch in diameter.

26. A stable emulsion or suspension of claim 23, wherein said grinding temperature is about 68° F.

27. A stable emulsion or suspension of claim 23, wherein said vitamin B-6 is present in an amount of about 1 to 500 ppm parts of said flax seed and said zinc ion is present in an amount of about 1 to 500 ppm parts of said flax seed.

28. A stable emulsion or suspension of claim 23, wherein said vitamin B-6 is present in an amount of about 50 to 250 ppm parts of said flax seed and said grinding temperature is about 68° F.

29. A stable emulsion or suspension of claim 23, wherein said solution is selected from the group consisting of water, milk, fruit juice, and vegetable juice.

30. A stable emulsion of claim 29, wherein said solution is water.

31. A stable emulsion or suspension of claim 23, wherein said soaking is form about 20 minutes.

32. A stable emulsion or suspension of claim 23, wherein said soaking temperature is about 68° F.

33. A stable emulsion or suspension of flax seed consisting essentially of ground flax seed, vitamin B-6, zinc ion, and an aqueous solution, wherein the emulsion or suspension remains chemically and physically stable for at least one week at a temperature of from about just above freezing to about 50° F.

34. A stable emulsion or suspension of flax seed consisting of ground flax seed, vitamin B-6, zinc ion, and an aqueous solution, wherein the emulsion or suspension remains chemically and physically stable for at least one week at a temperature from about just above freezing to about 50° F.

35. A stable emulsion or suspension of flax seed consisting essentially of ground flax seed, vitamin B-6, zinc ion, and an aqueous solution, wherein the emulsion or suspension remains chemically and physically stable after pasteurization for at least four weeks at a temperature of from about 26° F. to about 40° F.

36. A stable emulsion or suspension of flax seed consisting of ground flax seed, vitamin B-6, zinc ion, and an aqueous solution, wherein the emulsion or suspension remains chemically and physically stable after pasteurization for at least four weeks at a temperature of from about 26° F. to about 40° F.

37. A stable emulsion or suspension of flax seed consisting essentially of ground flax seed, vitamin B-6, zinc ion, and an aqueous solution, wherein the emulsion or suspension remains chemically and physically stable after sterilization for at least 3 months at a temperature of from about 26° F. to about 100° F.

38. A stable emulsion of suspension of flax seed consisting of ground flax seed, vitamin B-6, zinc ion, and an aqueous solution, wherein the emulsion or suspension remains chemically and physically stable after sterilization for at least 3 months at a temperature of from about 26° F. to about 100° F.

39. A stable emulsion or suspension of flax seed, comprising ground flax seed, vitamin B-6, zinc ion, and an aqueous solution, wherein fat globules in said emulsion or suspension have a size in the range of from about 0.05 to about 2.0 $\mu$.

40. A stable emulsion or suspension of flax seed comprising ground flax seed, vitamin B-6, zinc ion, and an aqueous solution, wherein fat globules in said emulsion or suspension have a size of about 0.05 $\mu$ or less.

41. A method of lower serum triglycerides cholesterol or both serum triglycerides and cholesterol comprising administering a therapeutically effective amount of a stable emulsion or suspension of flax seed produced by a method comprising:
 (1) grinding said flax seed in the presence of vitamin B-6 and zinc ion at a temperature of about 160° F. to just above freezing;
 (2) soaking said flax seed in an aqueous solution for about 10 minutes to overnight at a temperature of about 160° F. to just above freezing; and
 (3) blending or homogenizing said soaked, ground flax seed, with or without further additives, to form a stable emulsion or suspension;
 provided that the steps (1) and (2) can be conducted in any order.

42. A method of lowering serum triglycerides cholesterol or both serum triglycerides and cholesterol comprising administering a therapeutically effective amount of a stable emulsion or suspension of flax seed consisting essentially of ground flax seed, vitamin B-6, zinc ion, and an aqueous solution, wherein the emulsion or suspension remains chemically and physically stable for at least one week at a temperature of from about just above freezing to about 50° F.

43. A method of lowering serum triglycerides cholestrol or both serum triglycerides and cholesterol comprising administering a therapeutically effective amount of a stable emulsion or suspension of flax seed consisting of ground flax seed, vitamin B-6, zinc ion, and an aqueous solution, wherein the emulsion or suspension remains chemically and physically stable for at least one week at a temperature of from about just above freezing to about 50° F.

44. A method of lowering serum triglycerides cholesterol or both serum triglycerides and cholesterol comprising adminstering a therapeutically effective amount of a stable emulsion or suspension of flax seed consisting essentially of ground flax seed, vitamin B-6, zinc ion, and an aqueous solution, wherein the emulsion or suspension remains chemically and physically stable after pasteurization for at least four weeks at a temperature of from about 26° F. to about 40° F.

45. A method of lowering serum triglycerides cholesterol or both serum triglycerides and cholesterol comprising administering a therapeutically effective amount of a stable emulsion or suspension of flax seed consisting of ground flax seed, vitamin B-6, zinc ion, and an aqueous solution, wherein the emulsion or suspension remains chemically and physically stable after pasteurization for at least four weeks at a temperature of from about 26° F. to about 40° F.

46. A method of lwoering serum triglycerides cholesterol or both serum triglycerides and cholesterol comprising administering a therapeutically effective amount of a stable emulsion or suspension of flax seed consisting essentially of ground flax seed, vitamin B-6, zinc ion, and an aqueous solution, wherein the emulsion or suspension remains chemically and physically stable after sterilization for at least 3 months at a temperature of from about 26° F. to about 100° F.

47. A method of lower serum triglycerides cholesterol or both serum triglycerides and cholesterol comprising administering a therapeutically effective amount of a stable emulsion or suspension of flax seed consisting of ground flax seed, vitamin B-6, zinc ion, and an aqueous solution, wherein the emulsion or suspension remains chemically and physically stable after sterilization for at least 3 months at a temperature of from about 26° F. to about 100° F.

48. A method of lowering serum triglycerides and/or cholesterol or both serum triglycerides and cholesterol comprising administering a therapeutically effective amount of a stable emulsion or suspension of flax seed, comprising ground flax seed, vitamin B-6, zinc ion, and an aqueous solution, wherein fat globules in said emulsion or suspension have a size in the range of from about 0.05 to about 2.0 $\mu$.

49. A method of lowering serum triglycerides and/or cholesterol or both serum triglycerides and cholesterol comprising administering a therapeutically effective amount of a stable emulsion or suspension of flax seed comprising ground flax seed, vitamin B-6, zinc ion, and an aqueous solution, wherein fat globules in said emulsion or suspension have a size of about 0.05 $\mu$ or less.

* * * * *